US008876836B2

(12) United States Patent
Beyersdorff et al.

(10) Patent No.: US 8,876,836 B2
(45) Date of Patent: Nov. 4, 2014

(54) INSERTION INSTRUMENT FOR AN INTERVERTEBRAL IMPLANT

(71) Applicant: DePuy Synthes Products, LLC, Raynham, MA (US)

(72) Inventors: Boris Beyersdorff, Berlin (DE); Thierry Marnay, Montpellier (FR)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/960,104

(22) Filed: Aug. 6, 2013

(65) Prior Publication Data
US 2013/0317616 A1 Nov. 28, 2013

Related U.S. Application Data

(60) Continuation of application No. 11/512,327, filed on Aug. 30, 2006, now Pat. No. 8,535,326, which is a
(Continued)

(51) Int. Cl.
A61B 17/70 (2006.01)
A61B 17/02 (2006.01)
(Continued)

(52) U.S. Cl.
CPC ....... *A61F 2/4611* (2013.01); *A61B 2017/0256* (2013.01); *A61F 2002/4687* (2013.01); *A61F*
(Continued)

(58) Field of Classification Search
CPC ............ A61B 17/70; A61B 2017/0256; A61F 2002/443; A61F 2002/30904; A61F 2002/30808; A61F 2002/4628; A61F 2002/30604; A61F 2002/30383; A61F 2002/4687; A61F 2002/4681; A61F 2002/4627; A61F 2002/4622; A61F 2002/30884; A61F 2002/30662; A61F 2002/30892; A61F 2002/30841; A61F 2/4611; A61F 2/4425; A61F 2220/0025
USPC ......... 606/246, 279, 86 R, 90, 99, 105, 86 A; 623/17.11, 17.14, 17.15, 17.16
See application file for complete search history.

(56) References Cited

U.S. PATENT DOCUMENTS 114,816 A 5/1871 Hiestand
3,486,505 A * 12/1969 Morrison ........................ 606/90
(Continued)

FOREIGN PATENT DOCUMENTS

DE 2263842 A1 7/1974
DE 2804936 A1 8/1979
(Continued)

OTHER PUBLICATIONS

In the United States Patent and Trademark Office, in Re. U.S. Appl. No. 10/070,823, Examiner Interview Summary Record and Notice of Allowability dated Jul. 13, 2006.
(Continued)

Primary Examiner — Pedro Philogene
Assistant Examiner — David Comstock
(74) Attorney, Agent, or Firm — Baker & Hostetler LLP

(57) ABSTRACT

In an insertion instrument for a three-piece intervertebral implant that includes an upper part that can be placed against a vertebra, a lower part that can be placed against the adjacent vertebra, and a pivot element that can be inserted between these two parts, the instrument having two arms, disposed side by side and supported pivotably relative to one another on one end, which at their free ends each have one retention device for the upper part and lower part, respectively, of the intervertebral implant, it is proposed that a longitudinal guide for the pivot element is disposed in one of the arms.

22 Claims, 5 Drawing Sheets

Related U.S. Application Data division of application No. 10/070,823, filed as application No. PCT/EP99/06803 on Sep. 14, 1999, now Pat. No. 7,118,580.

(51) Int. Cl.
- *A61F 2/46* (2006.01)
- *A61F 2/44* (2006.01)
- *A61F 2/30* (2006.01)

(52) U.S. Cl.
CPC .......... 2002/443 (2013.01); *A61F 2002/30383* (2013.01); *A61F 2002/30904* (2013.01); *A61F 2002/30841* (2013.01); *A61F 2002/30884* (2013.01); *A61F 2002/4681* (2013.01); *A61F 2002/4627* (2013.01); *A61F 2/4425* (2013.01); *A61F 2002/4628* (2013.01); *A61F 2002/4622* (2013.01); *A61F 2002/30808* (2013.01); *A61F 2220/0025* (2013.01); *A61F 2002/30892* (2013.01); *A61F 2002/30604* (2013.01); *A61F 2002/30662* (2013.01)
USPC .......................................................... 606/99

(56) References Cited

U.S. PATENT DOCUMENTS

| | | |
|---|---|---|
| 3,579,829 A | 5/1971 | Sampson |
| 3,875,595 A | 4/1975 | Froning |
| 4,021,864 A | 5/1977 | Waugh |
| 4,034,746 A | 7/1977 | Williams |
| 4,038,897 A | 8/1977 | Murray et al. |
| 4,038,987 A | 8/1977 | Komiya |
| 4,232,404 A | 11/1980 | Samuelson et al. |
| 4,309,777 A | 1/1982 | Patil |
| 4,349,921 A | 9/1982 | Kuntz |
| 4,467,802 A | 8/1984 | Maslanka |
| 4,545,374 A | 10/1985 | Jacobson |
| 4,697,586 A | 10/1987 | Gazale |
| 4,714,469 A | 12/1987 | Kenna |
| 4,736,738 A | 4/1988 | Lipovsek et al. |
| 4,759,766 A | 7/1988 | Buettner-Janz et al. |
| 4,863,476 A | 9/1989 | Shepperd |
| 4,898,161 A | 2/1990 | Grundei |
| 4,946,378 A | 8/1990 | Hirayama et al. |
| 4,997,432 A | 3/1991 | Keller |
| 5,122,130 A | 6/1992 | Keller |
| 5,171,280 A | 12/1992 | Baumgartner |
| 5,211,645 A | 5/1993 | Baumgartner et al. |
| 5,228,455 A | 7/1993 | Barcel |
| 5,236,460 A | 8/1993 | Barber |
| 5,258,031 A | 11/1993 | Salib et al. |
| 5,306,308 A | 4/1994 | Gross et al. |
| 5,306,309 A | 4/1994 | Wagner et al. |
| 5,314,477 A | 5/1994 | Marnay |
| 5,336,232 A | 8/1994 | Green et al. |
| 5,364,397 A | 11/1994 | Hayes et al. |
| 5,370,697 A | 12/1994 | Baumgartner |
| 5,383,888 A | 1/1995 | Zvenyatsky et al. |
| 5,395,317 A | 3/1995 | Kambin |
| 5,401,269 A | 3/1995 | Buttner-Janz et al. |
| 5,409,492 A | 4/1995 | Jones et al. |
| 5,423,825 A | 6/1995 | Levine |
| 5,425,773 A | 6/1995 | Boyd et al. |
| 5,431,658 A | 7/1995 | Moskovich |
| 5,443,514 A | 8/1995 | Steffee |
| 5,484,437 A | 1/1996 | Michelson |
| 5,489,307 A | 2/1996 | Kuslich et al. |
| 5,501,654 A | 3/1996 | Failla et al. |
| 5,505,732 A | 4/1996 | Michelson |
| 5,507,816 A | 4/1996 | Bullivant |
| 5,554,191 A | 9/1996 | Lahille et al. |
| 5,556,431 A | 9/1996 | Buttner-Janz et al. |
| 5,562,736 A | 10/1996 | Ray et al. |
| 5,562,738 A | 10/1996 | Boyd et al. |
| 5,571,109 A | 11/1996 | Bertagnoli |
| 5,676,701 A | 10/1997 | Yuan et al. |
| 5,702,469 A | 12/1997 | Whipple et al. |
| 5,716,415 A | 2/1998 | Steffee |
| 5,720,751 A | 2/1998 | Jackson |
| 5,722,977 A | 3/1998 | Wilhelmy |
| 5,776,199 A | 7/1998 | Michelson |
| 5,782,830 A | 7/1998 | Farris |
| 5,782,832 A | 7/1998 | Larsen et al. |
| 5,797,909 A | 8/1998 | Michelson |
| 5,824,094 A | 10/1998 | Serhan et al. |
| D401,335 S | 11/1998 | Koros et al. |
| 5,885,300 A | 3/1999 | Tokuhashi et al. |
| 5,888,226 A | 3/1999 | Rogozinski |
| 5,895,428 A | 4/1999 | Berry |
| 5,897,593 A | 4/1999 | Kohrs et al. |
| 5,899,901 A | 5/1999 | Middleton |
| 5,899,941 A | 5/1999 | Nishijima et al. |
| 5,951,564 A | 9/1999 | Schroder et al. |
| 6,006,174 A | 12/1999 | Lin et al. |
| 6,017,342 A | 1/2000 | Rinner |
| 6,033,405 A | 3/2000 | Winslow et al. |
| 6,036,692 A | 3/2000 | Burel et al. |
| 6,042,582 A | 3/2000 | Ray et al. |
| 6,059,790 A | 5/2000 | Sand et al. |
| 6,063,088 A | 5/2000 | Winslow |
| 6,080,155 A | 6/2000 | Michelson |
| 6,083,225 A | 7/2000 | Winslow et al. |
| 6,086,595 A | 7/2000 | Yonemura et al. |
| 6,096,038 A | 8/2000 | Michelson |
| 6,102,950 A | 8/2000 | Vaccaro |
| 6,110,179 A | 8/2000 | Flivik et al. |
| 6,113,602 A | 9/2000 | Sand |
| 6,113,637 A | 9/2000 | Gill et al. |
| 6,113,638 A | 9/2000 | Williams et al. |
| 6,117,174 A | 9/2000 | Nolan |
| 6,126,660 A | 10/2000 | Dietz |
| 6,126,674 A | 10/2000 | Janzen |
| 6,146,421 A | 11/2000 | Gordon et al. |
| 6,156,040 A | 12/2000 | Yonemura et al. |
| 6,159,215 A | 12/2000 | Urbahns et al. |
| 6,171,339 B1 | 1/2001 | Houfburg et al. |
| 6,174,311 B1 | 1/2001 | Branch et al. |
| 6,224,599 B1 | 5/2001 | Baynham et al. |
| 6,238,414 B1 | 5/2001 | Griffiths |
| 6,241,769 B1 | 6/2001 | Nicholson et al. |
| 6,261,296 B1 | 7/2001 | Aebi et al. |
| 6,270,498 B1 | 8/2001 | Michelson |
| 6,296,647 B1 | 10/2001 | Robioneck et al. |
| 6,309,421 B1 | 10/2001 | Pisharodi |
| 6,368,350 B1 | 4/2002 | Erickson et al. |
| 6,368,351 B1 | 4/2002 | Glenn et al. |
| 6,402,785 B1 | 6/2002 | Zdeblick et al. |
| 6,436,139 B1 | 8/2002 | Shapiro et al. |
| 6,440,142 B1 | 8/2002 | Ralph et al. |
| 6,440,168 B1 | 8/2002 | Cauthen |
| 6,440,169 B1 | 8/2002 | Elberg et al. |
| 6,447,547 B1 | 9/2002 | Michelson |
| 6,478,800 B1 | 11/2002 | Fraser et al. |
| 6,478,801 B1 | 11/2002 | Ralph et al. |
| 6,478,823 B1 | 11/2002 | Michelson |
| 6,500,206 B1 | 12/2002 | Bryan |
| 6,517,544 B1 | 2/2003 | Michelson |
| 6,558,424 B2 | 5/2003 | Thalgott |
| 6,565,574 B2 | 5/2003 | Michelson |
| 6,595,995 B2 | 7/2003 | Zdelblick et al. |
| 6,599,294 B2 | 7/2003 | Fuss et al. |
| 6,610,065 B1 | 8/2003 | Branch et al. |
| 6,613,091 B1 | 9/2003 | Zdelblick et al. |
| 6,635,060 B2 | 10/2003 | Hanson et al. |
| 6,641,582 B1 | 11/2003 | Hanson et al. |
| 6,652,533 B2 | 11/2003 | O'Neil |
| 6,652,534 B2 | 11/2003 | Zucherman et al. |
| 6,712,819 B2 | 3/2004 | Zucherman et al. |
| 6,712,825 B2 | 3/2004 | Aebi et al. |
| 6,733,505 B2 | 5/2004 | Li |
| 6,746,454 B2 | 6/2004 | Winterbottom et al. |
| 6,755,841 B2 | 6/2004 | Fraser et al. |
| 6,770,074 B2 | 8/2004 | Michelson |

(56) References Cited

U.S. PATENT DOCUMENTS

| | | | |
|---|---|---|---|
| 6,824,565 | B2 | 11/2004 | Muhanna et al. |
| 6,875,213 | B2 | 4/2005 | Michelson |
| 6,896,676 | B2 | 5/2005 | Zubok et al. |
| 6,936,071 | B1 | 8/2005 | Marnay et al. |
| 6,964,687 | B1 | 11/2005 | Bernerd et al. |
| 6,966,912 | B2 | 11/2005 | Michelson |
| 7,081,120 | B2 | 7/2006 | Li et al. |
| 7,118,580 | B1 | 10/2006 | Beyersdorff et al. |
| 7,169,182 | B2 | 1/2007 | Errico et al. |
| 7,204,852 | B2 | 4/2007 | Marnay et al. |
| 7,238,203 | B2 | 7/2007 | Bagga et al. |
| 7,252,673 | B2 | 8/2007 | Lim |
| 7,491,204 | B2 | 2/2009 | Marnay |
| 7,547,309 | B2 | 6/2009 | Bertagnoli et al. |
| 7,575,576 | B2 | 8/2009 | Zubok et al. |
| 8,535,326 | B2 | 9/2013 | Beyersdorff et al. |
| 2002/0016633 | A1 | 2/2002 | Lin et al. |
| 2002/0049497 | A1 | 4/2002 | Mason |
| 2002/0072752 | A1 | 6/2002 | Zucherman et al. |
| 2002/0077702 | A1 | 6/2002 | Castro |
| 2002/0165612 | A1 | 11/2002 | Gerber et al. |
| 2003/0069586 | A1 | 4/2003 | Errico et al. |
| 2003/0083747 | A1 | 5/2003 | Winterbottom et al. |
| 2003/0135275 | A1 | 7/2003 | Garcia et al. |
| 2003/0208273 | A1 | 11/2003 | Eisermann et al. |
| 2004/0030387 | A1 | 2/2004 | Landry et al. |
| 2004/0143332 | A1 | 7/2004 | Krueger et al. |
| 2004/0215198 | A1 | 10/2004 | Marnay et al. |
| 2004/0225295 | A1 | 11/2004 | Zubok et al. |
| 2005/0021042 | A1 | 1/2005 | Marnay et al. |
| 2005/0143747 | A1 | 6/2005 | Zubok et al. |
| 2005/0143749 | A1 | 6/2005 | Zalenski et al. |
| 2005/0165408 | A1 | 7/2005 | Puno et al. |
| 2005/0228500 | A1 | 10/2005 | Kim et al. |
| 2005/0251260 | A1 | 11/2005 | Gerber et al. |
| 2006/0030856 | A1 | 2/2006 | Drewry et al. |
| 2006/0030860 | A1 | 2/2006 | Peterman |
| 2006/0064100 | A1 | 3/2006 | Bertagnoli et al. |
| 2006/0089656 | A1 | 4/2006 | Allard et al. |
| 2006/0100633 | A1 | 5/2006 | Michelson |
| 2006/0149273 | A1 | 7/2006 | Ross et al. |
| 2006/0241641 | A1 | 10/2006 | Albans et al. |
| 2007/0162134 | A1 | 7/2007 | Marnay |

FOREIGN PATENT DOCUMENTS

| | | |
|---|---|---|
| DE | 3526742 A1 | 1/1987 |
| DE | 4328690 B4 | 3/1995 |
| DE | 29916078 U1 | 11/1999 |
| EP | 0077159 A1 | 4/1983 |
| EP | 0471821 B1 | 2/1992 |
| EP | 0333990 B1 | 7/1993 |
| EP | 0712607 B1 | 2/2002 |
| FR | 2737656 | 8/1995 |
| FR | 2718635 A1 | 10/1995 |
| FR | 2795945 A1 | 1/2001 |
| JP | 2-261446 A | 10/1990 |
| WO | WO 91/13598 A1 | 9/1991 |
| WO | WO 98/34552 A1 | 8/1998 |
| WO | WO 01/01893 | 1/2001 |
| WO | WO 01/19295 A1 | 3/2001 |
| WO | WO 02/071986 A2 | 9/2002 |
| WO | WO 03/053290 A1 | 7/2003 |

OTHER PUBLICATIONS

In the United States Patent and Trademark Office, in Re. U.S. Appl. No. 10/070,823, Final rejection dated Aug. 23, 2005.
In the United States Patent and Trademark Office, in Re. U.S. Appl. No. 10/070,823, Non-final office action dated Sep. 23, 2004.
In the United States Patent and Trademark Office, in Re. U.S. Appl. No. 10/318,078, Final rejection dated Aug. 1, 2006.
In the United States Patent and Trademark Office, in Re. U.S. Appl. No. 10/318,078, Final rejection dated Nov. 12, 2004.
In the United States Patent and Trademark Office, in Re. U.S. Appl. No. 10/318,078, Non-final office action dated Apr. 21, 2004.
In the United States Patent and Trademark Office, in Re. U.S. Appl. No. 10/318,078, Non-final office action dated Aug. 8, 2005.
In the United States Patent and Trademark Office, in Re. U.S. Appl. No. 10/318,078, Notice of Allowability dated Feb. 26, 2007.
In the United States Patent and Trademark Office, In Re. U.S. Appl. No. 10/622,535, filed Jul. 21, 2003: Notice of Allowance dated Jul. 20, 2009.
In the United States Patent and Trademark Office, In Re. U.S. Appl. No. 10/622,535, filed Jul. 21, 2003: Non final office action dated Feb. 6, 2009.
In the United States Patent and Trademark Office, In Re. U.S. Appl. No. 10/622,535, filed Jul. 21, 2003: Non final office action dated Jan. 31, 2008.
In the United States Patent and Trademark Office, In Re. U.S. Appl. No. 10/622,535, filed Jul. 21, 2003: Non final office action dated Apr. 26, 2007.
In the United States Patent and Trademark Office, In Re. U.S. Appl. No. 10/622,535, filed Jul. 21, 2003: Non final office action dated Nov. 8, 2006.
In the United States Patent and Trademark Office, In Re. U.S. Appl. No. 10/622,535, filed Jul. 21, 2003: final rejection dated May 23, 2006.
In the United States Patent and Trademark Office, In Re. U.S. Appl. No. 10/622,535, filed Jul. 21, 2003: Non final office action dated Aug. 30, 2005.
In the United States Patent and Trademark Office, In Re. U.S. Appl. No. 10/947,660, filed Sep. 23, 2004: Notice of Allowance dated Mar. 9, 2009.
In the United States Patent and Trademark Office, In Re. U.S. Appl. No. 10/947,660, filed Sep. 23, 2004: Notice of Allowance dated Feb. 9, 2009.
In the United States Patent and Trademark Office, In Re. U.S. Appl. No. 10/947,660, filed Sep. 23, 2004: Non-Final Office Action dated Jul. 24, 2008.
In the United States Patent and Trademark Office, In Re. U.S. Appl. No. 10/947,660, filed Sep. 23, 2004: Non-Final Office Action dated Dec. 26, 2007.
In the United States Patent and Trademark Office, In Re. U.S. Appl. No. 10/947,660, filed Sep. 23, 2004: Non-Final Office Action dated Jul. 2, 2007.
In the United States Patent and Trademark Office, In Re. U.S. Appl. No. 10/947,660, filed Sep. 23, 2004: Non-Final Office Action dated Dec. 11, 2006.
In the United States Patent and Trademark Office, in Re. U.S. Appl. No. 10/070,823, Advisory Action dated Jun. 22, 2006.
In the United States Patent and Trademark Office, In Re. U.S. Appl. No. 10/622,535, filed Jul. 21, 2003: Non final office action dated Sep. 12, 2007.
In the United States Patent and Trademark Office, In Re. U.S. Appl. No. 10/622,535, filed Jul. 21, 2003: Notice of Allowance dated Nov. 17, 2009.
In the United States Patent and Trademark Office, in Re. U.S. Appl. No. 10/318,078, Advisory Action dated Dec. 29, 2006.
In the United States Patent and Trademark Office, in Re. U.S. Appl. No. 10/318,078, Advisory Action dated Mar. 28, 2005.
Derwent abstract of cited reference to Gau, FR2737656 A1, 2 pages (1997).

\* cited by examiner

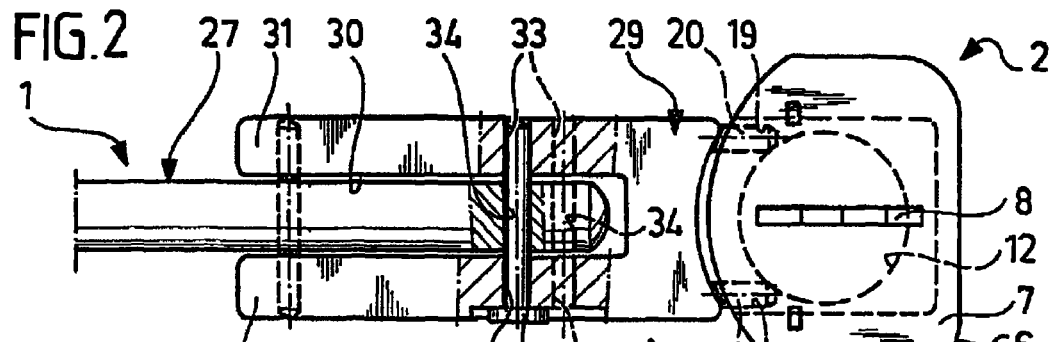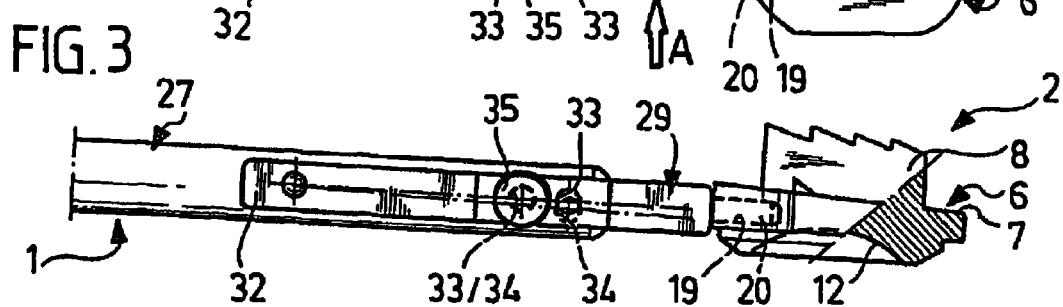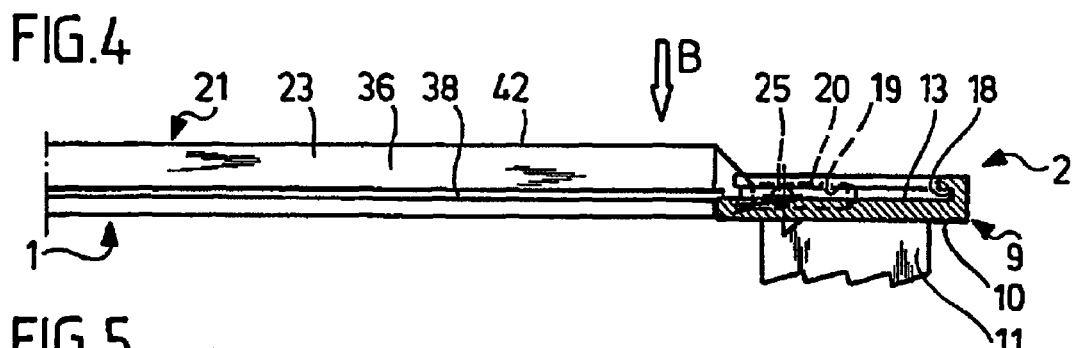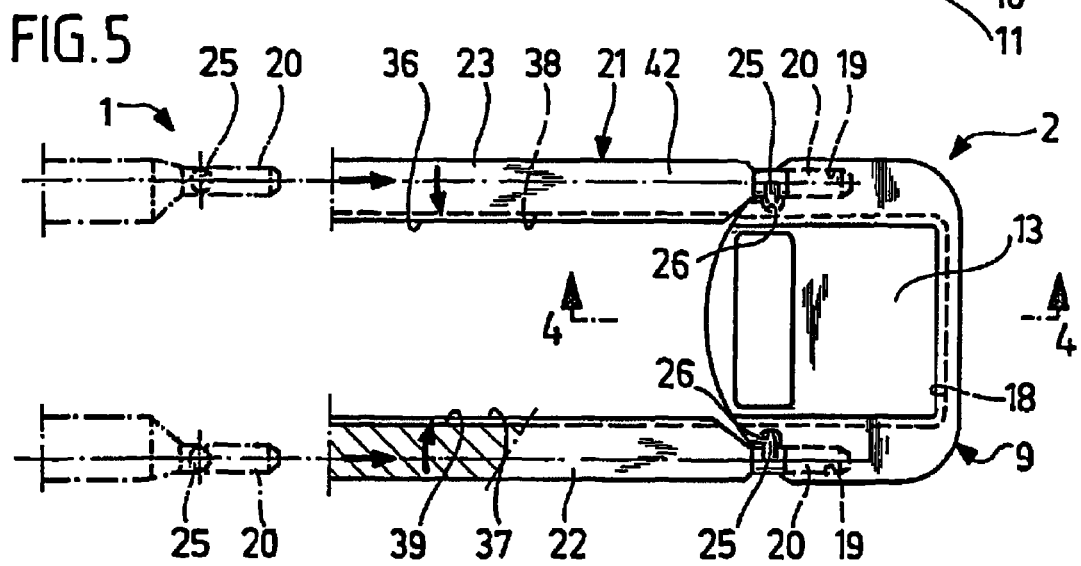

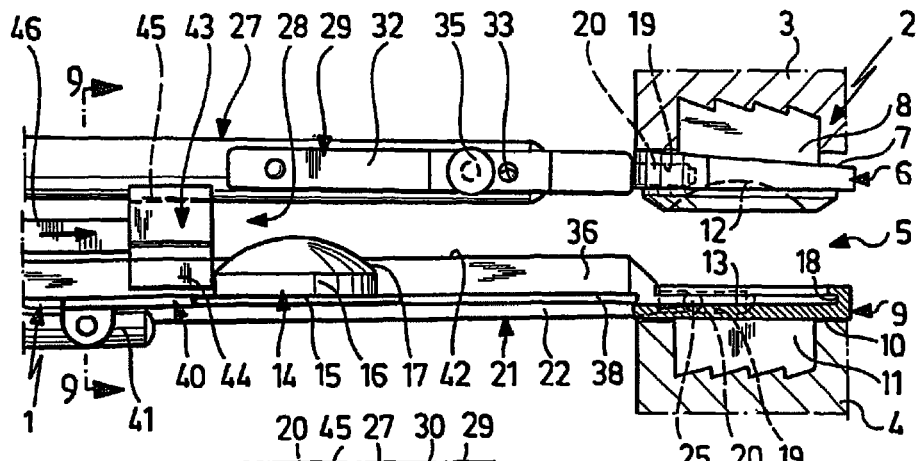
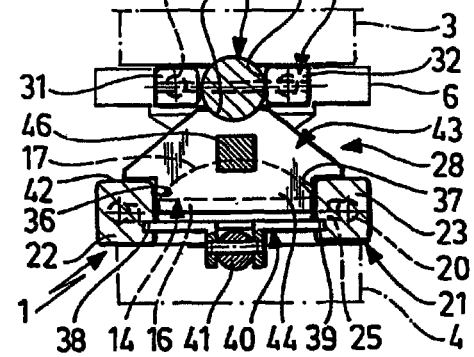
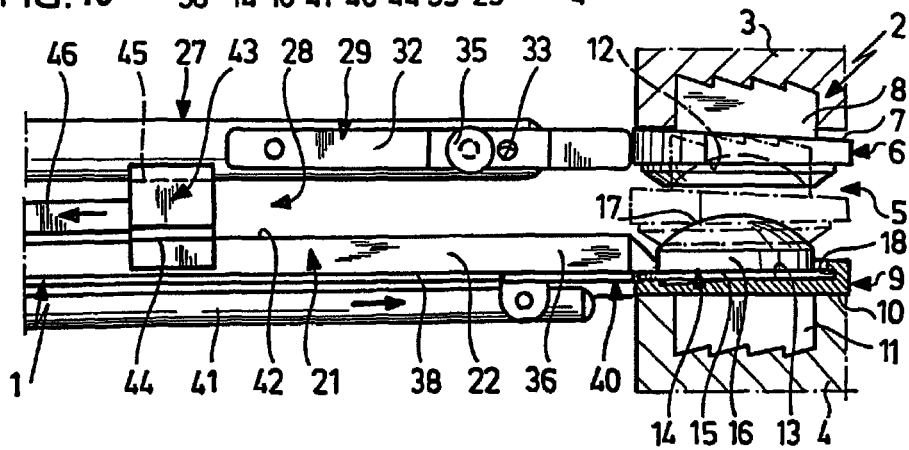

INSERTION INSTRUMENT FOR AN INTERVERTEBRAL IMPLANT

CROSS REFERENCE TO RELATED APPLICATIONS

This application is a continuation application of U.S. patent application Ser. No. 11/512,327 filed Aug. 30, 2006 which is a divisional of application Ser. No. 10/070,823, filed Jul. 15, 2002, now U.S. Pat. No. 7,118,580 which issued on Oct. 10, 2006, which is the National Stage of International Application No. PCT/EP99/06803, filed Sep. 14, 1999, which are hereby incorporated by reference in their entireties.

SUMMARY

The invention relates to an insertion instrument for a three-piece intervertebral implant that includes an upper part that can be placed against a vertebra, a lower part that can be placed against the adjacent vertebra, and a pivot element that can be inserted between these two parts, having two arms or levers, disposed side by side and supported pivotably at one end relative to one another, and each having at its other, free end one retention device for the upper part and lower part, respectively, of the intervertebral implant. The insertion instrument is also referred to as a medical device installation tool.

One such insertion instrument is known for instance from U.S. Pat. No. 5,314,477. The insertion instrument is embodied in the manner of tongs and can also be used, after the insertion of the upper and lower parts of the intervertebral implant, to move the two vertebrae apart to gain space for introducing the pivot element. In this known instrument, this pivot element must be introduced into the space between the upper and lower parts of the intervertebral implant by using other instruments. This is a difficult process in which there is the risk that the pivot element will be introduced tilted relative to the other two parts of the implant and will thus be damaged.

For inserting complete intervertebral implants, it is also known to move them along a longitudinal guide as far as the implant point and then to feed them out of the guide into the intervertebral space (U.S. Pat. No. 5,571,109). Such an instrument is suitable only for inserting complete intervertebral implants; moreover, the problem arises of an accurate adjustment of this guide relative to the intervertebral space: if there are maladjustments, the intervertebral implant could be inserted skewed, which can cause injuries.

It is the object of the invention to provide an insertion instrument, which may also be referred to as a medical device installation tool, of the type generically defined at the outset in such a way that these disadvantages are avoided and the introduction of the pivot element is simplified.

According to the invention, in an insertion instrument of the type described, this object is attained in that a longitudinal guide for the pivot element is disposed in one of the arms.

What is obtained thereby is a combined insertion instrument, which is used first to manipulate the upper and lower parts of the implant, and with which the upper and lower parts can be brought to the desired position inside the intervertebral space. As a result of the pivotable support of the arms, the upper part and lower part can then be moved apart from one another in a manner known per se, when the pivot axis acts as a fulcrum thus widening the intervertebral space, so that an introduction space for the pivot element is created between these parts. The pivot element is then inserted directly into this introduction space via the guide in one of the two arms, also known as levers, of the insertion instrument; by the connection of the two arms of the insertion instrument with the parts of the implant inserted into the intervertebral space, a reliable adjustment of the longitudinal guide for the pivot element is assured; moreover, it is assured that the pivot element will be introduced into the intervertebral space exactly in the desired relative position to the other two parts of the implant.

Both the insertion of the upper part and lower part of the implant and the introduction of the pivot element can thus be done with a single instrument; it is no longer necessary to disengage an instrument and replace it with another instrument; this insertion instrument performs a greater number of functions, namely that of inserting the upper part and lower part of the intervertebral implant, that of widening the intervertebral space, and finally that of introducing the pivot element into the space between the upper part and lower part of the implant.

It is favorable if the longitudinal guide is formed by protrusions engaging longitudinal grooves.

For instance, it can be provided that grooves opposite one another, which are engaged by lateral protrusions of the pivot element, are disposed in one of the arms, in a receiving chamber for the pivot element, the receiving chamber extending in the longitudinal direction of the arm.

In an especially preferred embodiment, it is provided that the arm or lever having the longitudinal guide has two rodlike legs, disposed parallel to and spaced apart from one another, and which between them form a receiving chamber for the pivot element and which guide the pivot element between them longitudinally of the receiving chamber.

It is favorable if the longitudinal guide, on its end adjacent to the pivotally supported end of the arms, forms an insertion region, where the pivot element can be inserted into the longitudinal guide. This insertion region can for instance be formed in such a way that longitudinal grooves are open at the face end; in another exemplary embodiment, it can be provided that the longitudinal guide does not begin until at a distance from the pivotally supported end that corresponds to the length of the pivot element to be inserted.

In an especially preferred embodiment, the longitudinal guide of the one arm changes over into a longitudinal guide of the part of the intervertebral implant that is retained on that arm. A continuous longitudinal guide for the pivot element is thus obtained on the one hand along the arm and on the other hand also along the first part of the intervertebral implant, so that an absolutely precise introduction of the pivot element into the attached part of the intervertebral implant is assured. During the insertion process, this part of the implant connected to the arm practically forms a part of the insertion instrument; after the introduction of the pivot element, this part is detached from the insertion instrument and remains in the intervertebral space as part of the implant.

In a further preferred embodiment, the insertion instrument includes a push member or pusher block, which is insertable into the longitudinal guide and is joined to a rodlike thrust element or pusher rod. Using this member, the pivot element can be advanced as far as the intervertebral space along the longitudinal guide.

It is especially advantageous if, according to a preferred embodiment of the invention, the two arms are disposed side by side at their free ends, in such a way that the retention devices overlap one another in the direction of the pivoting motion of the arms. As a result, a very low structural height of the insertion instrument, which is on the order of magnitude of the gap width of the intervertebral space, can be achieved, and it is furthermore possible as a result for the two parts of the implant, which are joined by the arms of the insertion instrument, to be guided quite close together and as a result to achieve a very low structural height. In this way, these two parts of the implant can be introduced into the intervertebral space without major widening of the intervertebral space; the widening of the intervertebral space takes place only after these parts of the intervertebral implant have been introduced, by the pivoting apart of the arms that hold these two parts of the implant.

It is advantageous if the pivotally supported ends of the two arms, i.e., the proximal handle portion of the arms or levers, have a spacing from one another such that the arms, in their insertion position of the upper part and the lower part of the intervertebral implant, in which the free ends of the arms, i.e., the distal portion of the arms or levers, are at their closest proximity to one another, have a greater spacing from one another on the supported end than on the free end. Once again, this contributes to making the structural height of the insertion instrument, and the implant parts retained in it during insertion, as slight as possible.

Also in this arrangement according to a preferred embodiment, it is possible to provide a spreader element, which is braced on both arms and can be fed or advanced along the arms in the direction toward the free end of the arms, and in the process pivotally spreads the arms apart. Thus solely by advancing the spreader element along the arms, the widening of the intervertebral space is made possible, once the upper and lower parts of the intervertebral implant have been inserted into the intervertebral space.

It is favorable if at least one of the two arms has a longitudinal guide for the spreader element, so that this element is guided in a defined way along the arms.

Furthermore, a feed rod, also referred to as a pusher rod, can be disposed on the spreader element, with the aid of which the spreader element is displaced along the arms.

In an especially preferred embodiment, the feed rod is embodied as a rack, which meshes with a driving gear wheel in the region of the pivotally supported ends of the arms; this provides a very sensitive feeding motion of the spreader element along the arms, and even major forces can be transmitted via the toothed connection.

The retention devices, with which the implant parts are retained in the arms, can be embodied in quite different ways; a design in which the retention devices are pins that engage openings of the upper part and lower part of the intervertebral implant, respectively, is especially preferred.

In a preferred embodiment, the retention devices on at least one of the arms are pivotable about a pivot axis that is located in the region of the free end of the arm and extends parallel to the pivot axis of the arm, and the retention devices, after being pivoted about this pivot axis, can be locked in different angular positions. As a result, it is possible to vary the inclination of the two implant parts relative to one another slightly, for instance in the range from 1 degree to 5 degrees, so that along with the implant height, the implant angle can also be selected to suit the correct positioning of the vertebrae.

In a preferred embodiment, for locking the angular position, a fixation pin can be provided, which can be inserted into bores oriented at different angular positions to one another.

In a further preferred embodiment, at least one retention device has a reasonable locking means. As a result of this reasonable locking means, the implant part retained on the arm is connected undetachably to the arm; only after this locking means is unlocked is it possible to separate the implant part from its insertion instrument.

As a result, unintentional separation of the insertion instrument from the implant parts is averted; it is even possible in this way for already-implanted implant parts to be pulled back out of the intervertebral space, should that be necessary.

It is favorable if the locking is effected by rotating a locking bar about an axis of rotation, which axis extends substantially parallel to the longitudinal axis of the arm on which the retention device is disposed.

In particular, in a preferred embodiment, the arm carrying the retention device, or a part of this arm, is rotatable about its longitudinal axis and carries a locking bar, which in one position non-releasably locks the part of the intervertebral implant retained on the retention device to the arm on which the retention device is disposed and in another position releases it.

An especially advantageous embodiment is obtained if the retention device is a pin engaging a receiving bore on the retained part of the intervertebral implant, and the locking bar is a protrusion protruding laterally from this pin, which in one angular position of the pin engages a corresponding recess of the implant part, but in another angular position emerges from this recess.

In an especially preferred embodiment, the arm having the longitudinal guide has two parallel legs, wherein the space between them forms a receiving chamber for the pivot element, and the other arm extends centrally between these legs, so that its free end can move between the legs.

It can furthermore be provided that a spreader element, disposed between the arms and displaceable along them, rests on the surface of the two legs and, with its protrusion, it reaches between the two legs to engage the receiving chamber. As a result, guidance of the spreader element along the arms is obtained.

In addition, the spreader element, on its top, can have an indentation into which the arm moves. Once again, this contributes to the guidance of the spreader element.

The legs of the one arm can be rectangular in cross section; the other arm can be circular in cross section.

BRIEF DESCRIPTION OF THE DRAWINGS

The ensuing description of preferred embodiments of the invention serves the purpose of more detailed explanation in conjunction with the drawing.

FIG. 2 is a top plan view on the upper arm of the insertion instrument of FIG. 1 with the upper part of the intervertebral implant retained on it;

FIG. 3 is a side view in the direction of the arrow A in FIG. 2;

FIG. 4 is a side view, taken along line 44 of FIG. 5, of the lower arm with the lower part of the intervertebral implant retained on it;

FIG. 5 is a top plan view of the lower arm, taken in the direction of the arrow B in FIG. 4;

FIG. 8 is a side view of the insertion instrument of FIG. 7, shortly before the insertion of the pivot element between the upper part and lower part of the intervertebral implant;

FIG. 9 is a sectional view taken along the line 9-9 in FIG. 8; and

FIG. 10 is a view similar to FIG. 8 after the insertion of the pivot element between the upper part arid lower part of the intervertebral implant.

DETAILED DESCRIPTION OF ILLUSTRATIVE EMBODIMENTS

Figure 1:
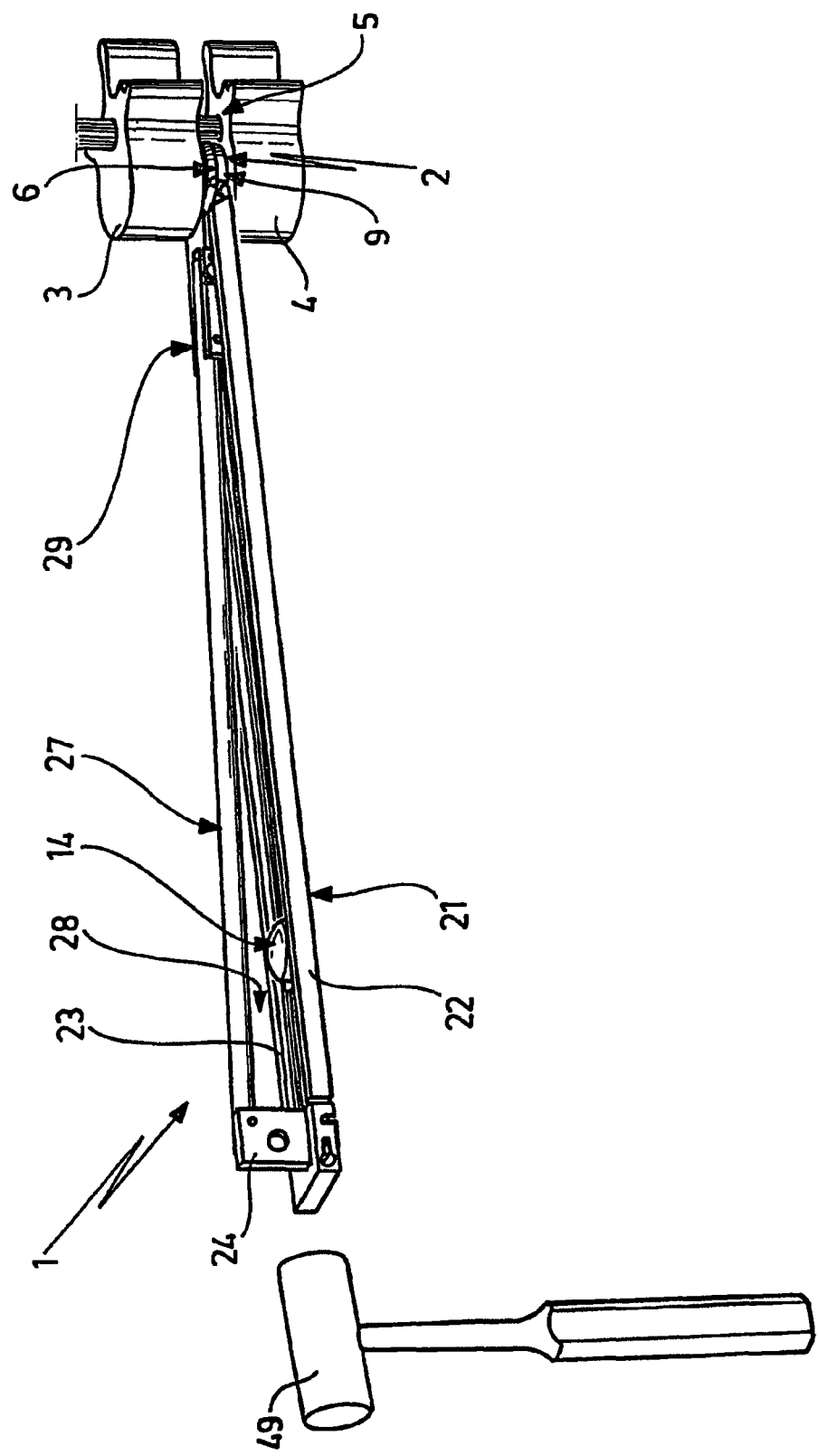
FIG. 1 is a perspective view of the insertion instrument after the introduction of the upper part and lower part of an intervertebral implant into the intervertebral space, before the spreading of the intervertebral space and before the introduction of the pivot element into the intervertebral space.

The insertion instrument 1 shown in the drawing is used to insert an intervertebral implant 2 into the intervertebral space 5 defined by two vertebrae 3, 4.

The intervertebral implant 2 includes a substantially plate-shaped upper part 6. With an upper flat contact face 7 and anchoring elements 8 protruding from it, and an also plate-shaped lower part 9 with a flat outer contact face 10 and anchoring elements 11 protruding from that face.

The upper part 6, on its side toward the lower part 9, has a dome-shaped bearing face 12; an indentation 13 is machined into the lower part 9 and is open toward one side and forms an insertion space for a pivot element 14 that also forms part of the intervertebral implant 2. This pivot element 14 has a plate-shaped, substantially rectangular base 15 and a bearing protrusion 16, protruding centrally from it on one side, whose upper side forms a dome-shaped bearing face 17.

The pivot element 14 can be inserted into the indentation 13 from the open side; the lateral edges of the base 15 engage lateral grooves 18 in the lower part 9, so that the pivot element 14 can be inserted, guided along these grooves 18, into the indentation 13.

In the implanted state, the bearing face 17 engages the concave bearing face 12 of the upper part, so that the upper part 6 and lower part 9 are braced on one another via the pivot element and are pivotable relative to one another.

Both the upper part 6 and lower part 9, on one side face, have insertion bores 19, extending parallel to the respective contact faces 7 and 10, and retaining pins 20 of the insertion instrument 1 can be inserted into these bores.

This insertion instrument 1 has a first elongated arm or first lever 21 with two spaced-apart parallel legs 22, 23, which are each retained at one end rotatably about its longitudinal axis on a bearing block 24 which provides a fulcrum on the proximate handle portion of the first arm 21. Both legs 22 and 23 have a square cross section and form rodlike long elements, which on the free end, along the extension of the axis of rotation of the legs each carry one of the retaining pins 20.

On these retaining pins 20 of the legs 22 and 23, radially protruding locking bar protrusions 25 are also provided, which can be embodied for instance as pins inserted radially into the retaining pins 20; these inserted pins in one angular position of the legs 22 engage lateral recesses 26 of the lower part 9, and these recesses 26 are open toward the upper part 6, so that by rotating the legs 22 and 23 by 90 degrees, the locking bar protrusions 25 can be rotated in such a way that they emerge from the recesses 26. As long as the locking bar protrusions 25 are engaging the recesses 26, the legs 22 and 23, when the retaining pins 20 have been inserted into the insertion bores 19, are releasably connected to the lower part 9, but if the locking, bar protrusions 25 are rotated out of the recesses 26 by rotation of the legs 22 and 23, then the retaining pins 20 can be pulled out of the insertion bores 19, so that a displacement of the legs 22 and 23 relative to the lower part 9, and thus an insertion or separation become possible.

The legs 22 and 23 can be releasably fixed in their final positions by a detent engagement, not shown in the drawing, in which positions the locking bar protrusion 25 engages the recess 26 and emerges completely from the recess 26, respectively.

On the bearing block 24, spaced apart from the plane defined by the two legs 22 and 23, a second arm or lever 27 is pivotably supported about an axis of rotation that extends transversely to the longitudinal direction of the legs 22 and 23 and parallel to the plane defined by them; the arm 27 is disposed approximately midway between the two legs 22 and 23, so that the free end of the arm 27 can enter the space 28 between the two legs 22 and 23. Because of the spacing of the bearing location of the arm 27 from the plane defined by the legs 22 and 23, the spacing of the arm 27 from the arm 21 decreases continuously, as becomes clear from the illustration in FIG. 1, forming a fulcrum for turning of arm or lever 27 towards and away from the arm or levers 21. Together arms 21, 27 form two opposing levers of insertion instrument 1.

The arm 27 is circular in cross section and on its free end or distal portion it carries a U-shaped holder 29, which receives the free end of the arm 27 in the space 30 between two parallel legs 31, 32. In the region of the free end of the legs 31, 32, the holder 29 and the arm 27 are joined together in such a way that they can be pivoted about an axis of rotation extending parallel to the pivot axis of the arm 27. As a result, the holder 29 can assume different angular positions relative to the arm 27; in FIG. 3, two angular positions differing by a small angular amount are shown in dot-dashed lines. For fixing the holder 29 in different angular positions, transverse bores 33 and 34, respectively, are provided both in the legs 31 and 32 and in the arm 27, and specifically a plurality of such pairs of transverse bores are offset in the longitudinal direction and are oriented with one another at various positions of the holder 29 relative to the arm 27. A fixation-pin 35 can be inserted into these pairs of transverse bores 33, 34. Since in the various pairs the transverse bores 33, 34 that belong together can assume a different position, for each pair of transverse bores when a fixation pin 35 is inserted, a different angular position relative to the arm 27 results; the pivot angles are on the order of magnitude of a few degrees, and for instance a total range that can be between 1 degree and 5 degrees is covered.

Retaining pins 20 are disposed on the holder 29 and can be inserted as described into insertion bores 19 of the upper part 6. Because of the different angular position of the holder 29, it is possible to tilt the upper part 6 slightly relative to the lower part 9 that is retained on the legs 22 and 23.

Figure 6:
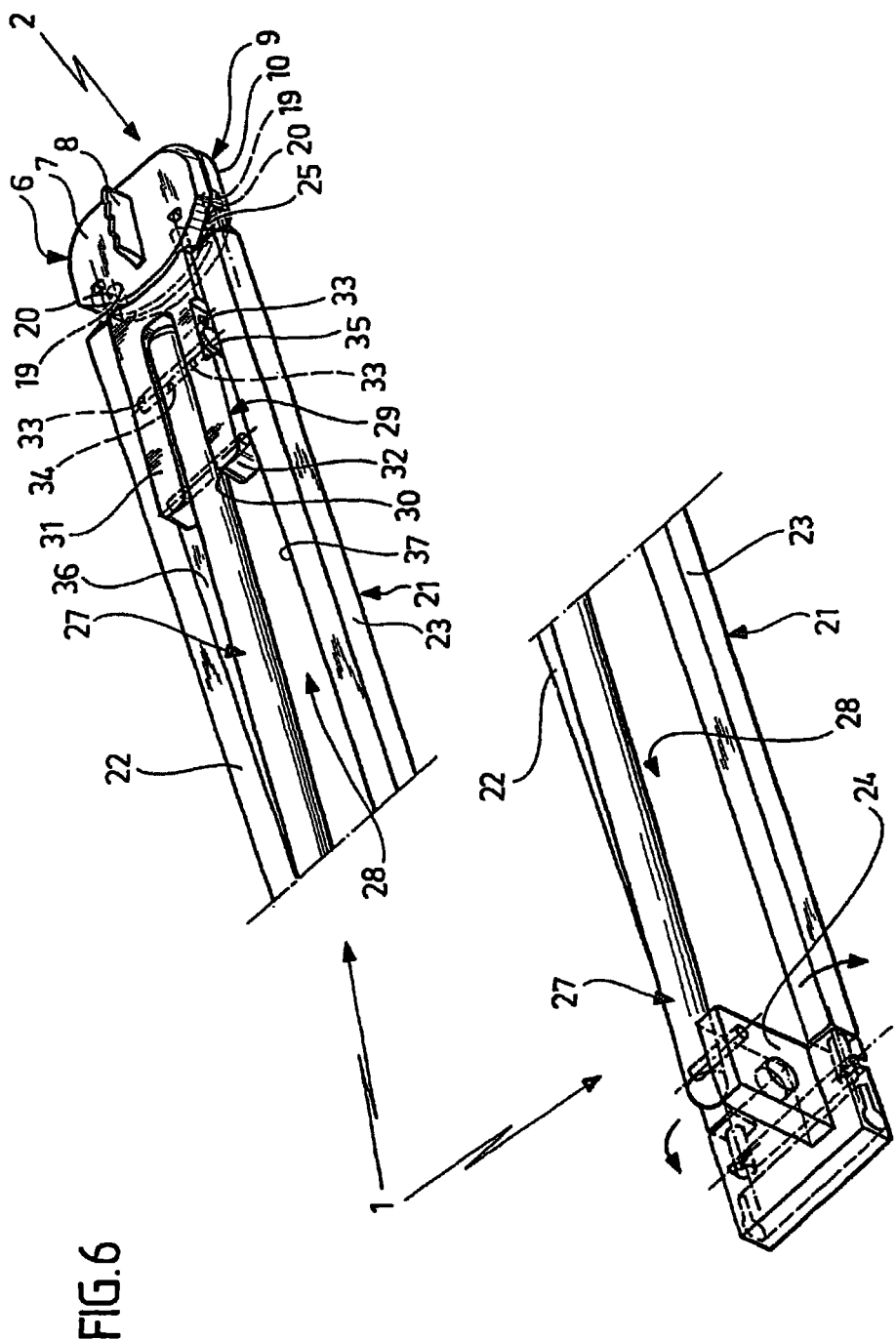
FIG. 6 is a perspective view of the insertion instrument with the upper part and lower part retained on it in the insertion position, with the implant parts at their closest proximity to one another.

The width of the holder 29 is selected such that the holder 29 fits into the space 28 between the two legs 22 and 23, so that the retaining pins 20 on the holder 29 and on the legs 22 and 23 can be disposed practically side by side; as a result, it is possible to retain the upper part 6 and lower part 9 in a position of closest proximity on the two arms 21 and 27; this position is designated as the insertion position (FIGS. 1 and 6).

When the locking bar protrusions 25 engage the recesses 26, the two legs 22 and 23, in the inside faces 36, 37 facing one another, have longitudinal grooves 38, 39, facing one another, which form a longitudinal guide for the pivot element 14. The dimensioning of these longitudinal grooves 38, 39 corresponds to that of the side edges of the base 15 of the pivot element 14, so that the pivot element 14 is guided longitudinally in the space 28 between the legs 22 and 23, when the side edges of the base 15 move into the longitudinal grooves 38 and 39. These longitudinal grooves 38 and 39 end at a distance in front of the bearing block 24 to enable an insertion of the base 15 into the longitudinal grooves 38, 39, and these longitudinal grooves 38 and 39 continue as far as the free end of the legs 22 and 23, where they merge directly with the grooves 18, disposed on both sides of the indentation 13, that serve to receive the base 15. What is thus obtained is a guide path for the pivot element 14 that leads from the legs 22 and 23 directly into the inside of the lower part 9 of the intervertebral implant 2.

A plate-like push member 40 (also referred to as a pusher block) is also insertable into the longitudinal grooves 38 and 39 and is pivotably connected to a pusher rod such as thrust rod 41. By means of this thrust rod 41, the pivot element 14, inserted into the longitudinal grooves 38 and 39, can be advanced along its guide path; to that end, the push member 40 is introduced after the pivot element 14 into the guide path formed by the longitudinal grooves 38 and 39.

A spreader element 43 that spans the space 28 between the two legs 22 and 23 is braced on the flat top side 42 of the legs 22 and 23; with a protrusion 44, it moves slightly into the space 28 and as a result is guided transversely to the longitudinal direction of the legs 22 and 23. This spreader element 43, on its end remote from the legs 22 and 23, has an indentation 45 of arclike cross section, into which the arm 27 moves. The spreader element 23 is connected to a thrust rod 46, embodied as a rack, which meshes with a gear wheel 47 that is supported rotatably on the bearing block 24 and can be rotated by means of a handle part 48 located at a proximal, handle portion of the opposed levers. Upon such rotation, the thrust rod 46 is displaced, which leads to a longitudinal displacement of the spreader element 43 along the legs 22 and 23. Upon such advancement of the spreader element 43, the arm 27 is as a result pivoted away from the legs 22 and 23; that is, the arms 27 and 21 (first and second levers) are spread apart via pivoting of their respective proximal handle portions about the fulcrum formed by bearing block 24, so that as a result the upper part 6 and lower part 9 are moved away from one another. This in turn leads to forcing the vertebrae 3 and 4 apart and thus to widening of the intervertebral space 5.

The insertion instrument described preferably comprises a biocompatible metal, such as titanium or a titanium alloy; the same is true for the upper part 6 and lower part 9 of the intervertebral implant 2. The pivot element 14 is made from a biocompatible plastic material, such as polyethylene, and the spreader element 43 is likewise preferably of a plastic material, so as to assure good sliding relative to the legs 22 and 23 and to the arm 27.

For insertion of the intervertebral implant 2 into an intervertebral space 5, first, after the disk has been removed from the intervertebral space 5, the intervertebral space is prepared in a suitable way; for instance, perpendicular grooves can be hammered into the vertebrae 3, 4 that receive the respective anchoring elements 8 and 11 of the intervertebral implant 2.

After suitable preparation, the upper part 6 and the lower part 9 are slipped onto the arms 27 and 21, respectively; the lower part 9 is locked to the arm 21 by rotation of the legs 22, 23, causing the locking bar protrusions 25 to engage the recesses 26 of the lower part 9 and the two arms 21 and 27 are pivoted into the insertion position, in which the upper part 6 and the lower part 9 are brought into their closest proximity; accordingly these two parts have a slight structural height. In this insertion position, the upper part 6 and lower part 9 are introduced into the prepared intervertebral space 5, for instance by being hammered in using a hammerlike instrument 49 (FIG. 1). The inclination that the upper part 6 assumes relative to the lower part 9 can be preselected by pivoting the holder 29 relative to the arm 27; in the desired position, the angular position is fixed by the fixation pin 35.

After this insertion of the upper part 6 and lower part 9, the pivot element 14 and the push member 40 are inserted successively into the guide path formed by the longitudinal grooves 38, 39; furthermore, both the push member 40 and the thrust rod 41 and the gear wheel 47 are inserted into the instrument.

Figure 7:
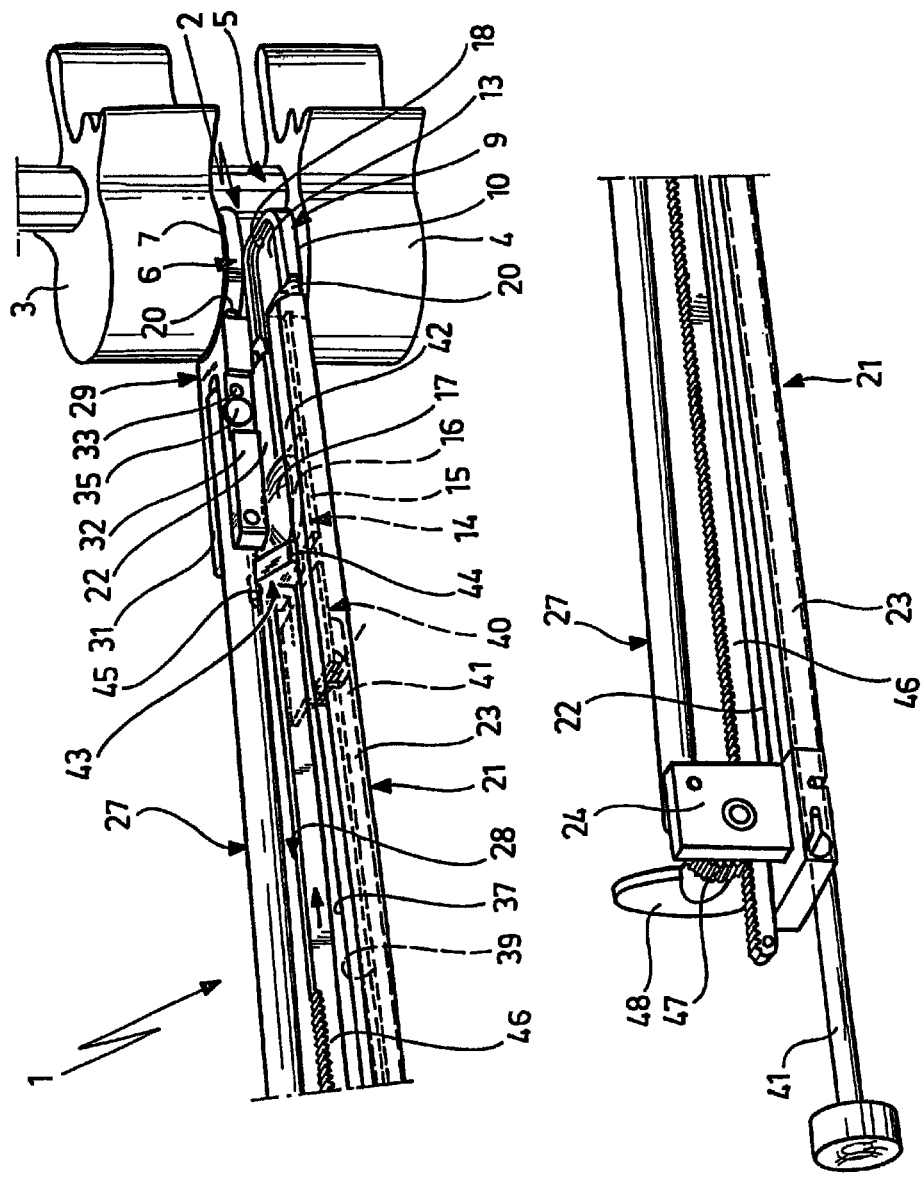
FIG. 7 is a perspective view of the insertion instrument of FIG. 6 after the insertion of the upper part and lower part of the intervertebral implant into the intervertebral space and after the widening of the intervertebral space, shortly before the pivot element is inserted between the upper part and lower part of the intervertebral implant.

By rotation of the gear wheel 47 and advancement of the spreader element 43, the arms 21 and 27 are spread apart; this leads to an increase in the mutual spacing between the upper part 6 and lower part 9, and thus to a widening of the intervertebral space 5 (FIGS. 7-9). The widening is selected to be so great enough that by means of the push member 40, the pivot element 14 can be inserted into the indentation 13 in the lower part 9 (FIG. 10). Following that, by retraction of the spreader element 43, the spacing between the upper part 6 and lower part 9 is reduced again, until the bearing faces 12 and 17 engage one another and the parts of the intervertebral implant 2 have thus attained their final position (FIG. 10, dot-dashed outline of upper part 6).

By rotation of the legs 22 and 23 about their longitudinal axes, the engagement of the locking bar protrusions 25 and the recesses 26 is undone, and then the insertion instrument 1 can be pulled off the now properly inserted intervertebral implant 2.

What is claimed:

1. A medical device installation tool, comprising:
    a first lever elongate in a first direction, the first lever having a first proximal portion and a first distal portion that is spaced from the first proximal portion in the first direction;
    a second lever having a second proximal portion and a second distal portion, the second lever being pivotable relative to the first lever about an axis of rotation;
    a spreader element configured to apply a force that causes the second lever to pivot relative to the first lever about the axis of rotation, the spreader element being translatable with respect to the first and second levers in the first direction to a first location that is between the first distal portion and the axis of rotation with respect to the first direction; and
    a push member including a pusher block and a pusher rod joined to the pusher block, such that the push member is translatable with respect to the first and second levers in the first direction, and the push member is also translatable with respect to the spreader element in the first direction to a second location that is between the first distal portion and the first location with respect to the first direction.

2. The medical device installation tool of claim 1, wherein the first distal portion includes a first retention member, the second distal portion includes a second retention member, the first and second retention members each configured to secure one of an upper element and a lower element of an implant to the respective lever, and the push member is configured to insert a middle element of the implant between the upper and lower elements.

3. The medical device installation tool of claim 2, wherein the middle element is a pivot element that permits relative movement between the upper and lower elements of the implant when the pivot element is inserted between the upper and lower elements of the implant.

4. The medical device installation tool of claim 3, wherein the pusher block is configured to translate the pivot element with respect to the first and second levers in the first direction.

5. The medical device installation tool of claim 4, wherein the spreader element includes a first surface that corresponds in shape to the first lever, and a second surface that corresponds in shape to the second lever, such that as the spreader element translates with respect to the first and second levers in the first direction, the first surface rides along the first lever and the second surface rides along the second lever thereby moving the first and second distal portions away from one another.

6. The medical device installation tool of claim 5, wherein the spreader element defines a height measured between the first and second surfaces along a second direction that is substantially perpendicular to the first direction, the height configured such that the spreader element defines a gap between the first and second levers, the gap being sized such that the pivot element contacts only one of the first and second levers as the pivot element is inserted between the upper and lower elements of the implant.

7. The medical device installation tool of claim 2, wherein the axis of rotation is a first axis of rotation, and at least one of the first and second retention members is rotatable relative to the other of the first and second retention members along a second axis of rotation that is substantially perpendicular to the first axis of rotation.

8. The medical device installation tool of claim 7, wherein rotation of the at least one of the first and second retention members secures the respective retention member within an aperture of one of the upper and lower elements to secure the respective lever to the respective element.

9. The medical device installation tool of claim 1, further comprising a fulcrum pivotally connecting the first and second proximal portions.

10. The medical device installation tool of claim 1, wherein the first and second levers are each movable independent of the other of the first and second levers.

11. The medical device installation tool of claim 1, wherein the first lever includes a pair of arms that each include an inner surface that faces the inner surface of the other of the pair of arms so as to define a gap between the pair of arms.

12. The medical device installation tool of claim 11, wherein the first and second levers are pivotable relative to each other about the axis of rotation between a closed configuration and an open configuration, such that in the closed configuration the distal portion of the second lever is positioned within the gap between the pair of arms of the first lever, and in the open configuration the distal portion of the second lever is outside the gap.

13. The medical device installation tool of claim 1, wherein the spreader element is configured to be positioned at least partially between the first and second levers.

14. The medical device installation tool of claim 1, wherein the push member is configured to be positioned at least partially between the first and second levers.

15. The medical device installation tool of claim 14, wherein the spreader element is configured to be positioned at least partially between the first and second levers.

16. A medical device installation tool comprising:
a first lever elongate in a first direction, the first lever including a pair of arms that are spaced apart from one another in a second direction, each of the pair of arms including an inner surface that faces the inner surface of the other of the pair of arms so as to define a gap between the pair of arms, each of the pair of arms having a supported end and a free end that is spaced from the respective supported end in the first direction;
a second lever having a supported end and a free end, the first and second levers being pivotable relative to each other about an axis of rotation between a closed configuration and an open configuration, the supported end of the second lever being closer to the axis of rotation than the free end;
wherein in the closed configuration the free end of the second lever is positioned: 1) between the free end of each of the pair of arms and the supported end of each of the pair of arms with respect to the first direction; and 2) within the gap between the pair of arms of the first lever with respect to the second direction, and in the open configuration the free end of the second lever is removed from the gap.

17. The medical device installation tool of claim 16, wherein the second direction is substantially perpendicular to the first direction.

18. The medical device installation tool of claim 17, further comprising a spreader element configured to be positioned at least partially between the first and second levers such that the spreader element is translatable with respect to the first and second levers in the first direction.

19. The medical device installation tool of claim 18, further comprising a push member configured to be positioned at least partially between the first and second levers, the push member including a pusher block and a pusher rod joined to the pusher block, such that the push member is translatable with respect to the first and second levers in the first direction, and the push member is also translatable with respect to the spreader element in the first direction.

20. The medical device installation tool of claim 16, wherein each of the pair of arms has a proximal portion and a distal portion that is spaced from the proximal portion in the first direction, the distal portion of each of the pair of arms includes a retention member configured to secure one of the upper and lower elements to the first lever, the second lever includes a proximal portion and a distal portion, and the distal portion of the second lever includes a retention member configured to secure the other of the upper and lower elements to the second lever.

21. The medical device installation tool of claim 20, wherein the axis of rotation is a first axis of rotation, and at least one of the retention members is rotatable relative to another of the retention members along a second axis of rotation that is substantially perpendicular to the first axis of rotation.

22. The medical device installation tool of claim 16, further comprising a fulcrum pivotally connecting the supported ends of the first and second levers such that the first and second levers are each movable independent of the other of the first and second levers.

* * * * *